(12) United States Patent
Leimkühler et al.

(10) Patent No.: US 6,706,913 B2
(45) Date of Patent: Mar. 16, 2004

(54) PROCESS FOR PREPARING (CYCLO) ALIPHATIC ISOCYANATES

(75) Inventors: Hans-Joachim Leimkühler, Leverkusen (DE); Herbert Stutz, Dormagen (DE); Helmut Schmidt, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/190,262

(22) Filed: Jul. 3, 2002

(65) Prior Publication Data

US 2003/0069441 A1 Apr. 10, 2003

(30) Foreign Application Priority Data

Jul. 11, 2001 (DE) .......................................... 101 33 728

(51) Int. Cl.7 ............................................ C07C 263/00
(52) U.S. Cl. ...................................................... 560/347
(58) Field of Search .......................................... 560/347

(56) References Cited

U.S. PATENT DOCUMENTS 4,847,408 A * 7/1989 Frosch et al. ................ 560/347
5,633,396 A * 5/1997 Bischof et al. .............. 560/347

FOREIGN PATENT DOCUMENTS

GB 1165831 * 10/1969

* cited by examiner

Primary Examiner—Joseph K. McKane
Assistant Examiner—Rei Tsang Shiao
(74) Attorney, Agent, or Firm—Joseph C. Gil; Thomas W. Roy; Gary F. Matz

(57) ABSTRACT

The present invention relates to a novel process for preparing (cyclo)aliphatic diisocyanates and triisocyanates by phosgenation of (cyclo)aliphatic diamines and triamines in the gas phase by accelerating the flow of at least one of reactants in the region where the reactants are mixed.

3 Claims, 1 Drawing Sheet

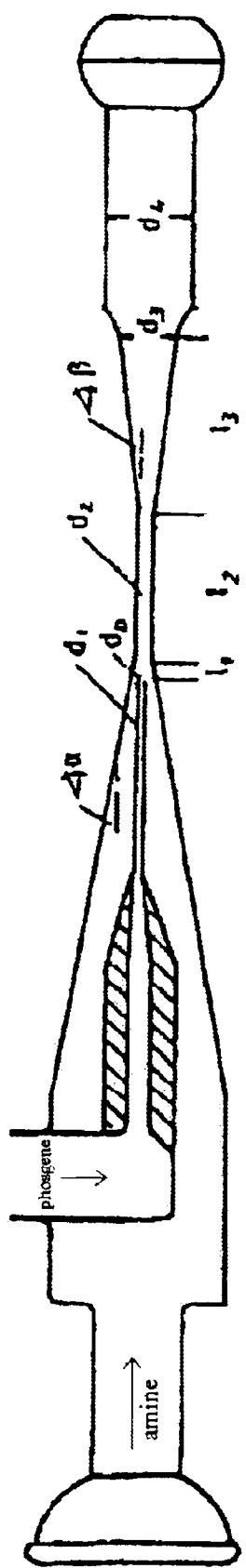
FIGURE

PROCESS FOR PREPARING (CYCLO) ALIPHATIC ISOCYANATES

FIELD OF THE INVENTION

The present invention relates to a process for preparing (cyclo)aliphatic diisocyanates and triisocyanates by the phosgenation of (cyclo)aliphatic diamines and triamines in the gas phase.

BACKGROUND OF THE INVENTION

It is known that diamines can be phosgenated in the gas phase. The phosgenation of (cyclo)aliphatic diamines in a tubular reactor equipped with a mechanical stirrer is described in GB-A 1 165 831. The reactor resembles a film evaporator in which the stirrer mixes the gases and at the same time brushes over the heated walls of the tubular reactor, in order to prevent a build-up of polymeric material on the wall of the pipe. However, the use of a high-speed stirrer when handling phosgene at a temperature of approximately 300° C. necessitates great expense on safety measures to seal the reactor and retain the stirrer in the highly corrosive medium.

EP-A 0 289 840 and EP-A 0 749 958 describe the phosgenation of (cyclo)aliphatic diamines using a cylindrical reaction chamber without moving parts, in which the reactants are reacted with one another while a turbulent flow is maintained. The management of the flow leads to back-mixing as a result of which the products react with the diamine starting material to form solid deposits. This leads to contamination of the reactor and blockages in the path of the gas.

It is an object of the present invention to produce (cyclo) aliphatic isocyanates by the gas-phase phosgenation of the corresponding amines while avoiding the previously mentioned disadvantages of prior art.

This object may be achieved with the process of the present invention by carrying out the reaction such that the flow of at least one of the reactants is accelerated in the region where the reactants are mixed together.

SUMMARY OF THE INVENTION

The present invention relates to a process for preparing a (cyclo)aliphatic diisocyanate or triisocyanate corresponding to the formula $$R—(NCO)_n \qquad (I),$$

wherein
R represents a (cyclo)aliphatic hydrocarbon group having up to 15 carbon atoms, provided that there are at least two carbon atoms between two nitrogens,
n represents the number 2 or 3, by
a) separately heating phosgene and a diamine or a triamine corresponding to the formula

$$R—(NH_2)_n \qquad (II),$$

to a temperature of 200° C. to 600° C., wherein the amine may optionally be diluted with an inert gas or with the vapors of an inert solvent,
b) accelerating the flow of at least one of the reactants in the region where the reactants are mixed and
c) continuously reacting the reactants in a reaction chamber that does not have moving parts.

BRIEF DESCRIPTION OF THE DRAWING

The FIGURE shows one embodiment of the reaction chamber according to the invention.

DETAILED DESCRIPTION OF THE INVENTION

Starting materials for the process according to the invention include (cyclo)aliphatic diamines or triamines corresponding to the formula

$$R—(NH_2)_n \qquad (II),$$

wherein
R represents a (cyclo)aliphatic hydrocarbon group having up to 15 carbon atoms, preferably 4 to 13 carbon atoms, provided that there are at least two carbon atoms between two amino groups,
n represents the number 2 or 3.

Examples of suitable (cyclo)aliphatic diamines include 1,4-diaminobutane, 1,6-diaminohexane, 1,11-diaminoundecane, 1,4-diaminocyclohexane, 1-amino-3,3,5-trimethyl-5-aminomethylcyclohexane (IPDA), 4,4'-diaminodicyclohexylmethane and 4,4'-diaminodicyclohexyl-propane-(2,2). An example of a suitable (cyclo)aliphatic triamine is 1,8-diamino-4-(aminomethyl)octane, triaminononane. Preferred amines are 1,6-diaminohexane, IPDA and 4,4'-diaminodicyclohexylmethane.

The products obtained from the phosgenation reaction are (cyclo)aliphatic diisocyanates or (cyclo)aliphatic triisocyanates corresponding to formula (I)

$$R—(NCO)_n \qquad (I),$$

wherein
R represents a (cyclo)aliphatic hydrocarbon group having up to 15 carbon atoms, preferably 4 to 13 carbon atoms, provided that there are at least two carbon atoms between two isocyanate groups.

Preferred diisocyanates are 1,6-diisocyanatohexane, 1-isocyanato-3,3,5-trimethyl-5-isocyanatomethylcyclohexane (IPDI) and 4,4'-diaminodicyclohexylmethane. Preferred triisocyanate is 1,8-diisocyanato-4-(isocyanatomethyl)octane, triisocyanatononane.

Before the process according to the invention is carried out, the starting diamines are vaporized and heated to 200° C. to 600° C., preferably 250° C. to 500° C., and passed to the reactor, optionally diluted with an inert gas (for example, $N_2$ or argon) and/or with the vapors of an inert solvent (for example, dichlorobenzene).

Before the process according to the invention is carried out, the phosgene used for the phosgenation reaction is heated to a temperature of 200° C. to 600° C., preferably 250° C. to 500° C.

Shortly before being mixed in the reactor, both reactants may be passed over torque-preparing baffles in order to stabilize the flow.

To carry out the process according to the invention, the preheated and optionally torque-laden flows of the amine or amine-inert gas and phosgene are passed continuously into a reaction chamber without moving parts. Prior to the mixing of the two streams of reactants, at least one of the streams, preferably phosgene, is accelerated. In the process the maximum velocity is attained within the range from one free flow diameter in front, to one free flow diameter behind, the mixing position. The maximum velocity is preferably attained at the position where the reactants are mixed.

One suitable embodiment of the process according to the invention is a rotationally symmetrical mixing tube having a cross-sectional area which is reduced in the region where the reactants are brought together and widens again in the section where the reaction takes place. This arrangement increases the rate of the gas flow. In a preferred embodiment of the process according to the invention, this reduction of the cross-sectional area with subsequent widening imitates the shape of a Venturi tube.

In another embodiment of the process according to the invention, in the direction of flow before the mixing of the two reactants, the reaction chamber is subjected to an external heating, whereby the reactants are heated and, due to the associated enlargement in volume at constant flow area, are accelerated to a higher velocity. A combination of a narrowing of the cross-section and external heating also leads to the favorable results according to the invention.

The reactors are preferably prepared from steel, glass, or alloyed or enamelled steel and are of a sufficient length to facilitate a complete reaction of the amine with phosgene under the process conditions. The gas flows are generally introduced into the reaction chamber at one end. This introduction can be effected, for example, through nozzles attached to one end of the reactor, or through a combination of nozzle and annular gap between nozzle and wall. The mixing zone is likewise maintained at a temperature of 200° C. to 600° C., preferably 250° C. to 500° C. This temperature is maintained, if necessary, by heating the reactor.

While the process according to the invention is being carried out, in general the pressure is preferably 200 mbar to 3000 mbar within the feed pipes to the reaction chamber and 150 mbar to 2000 mbar at the outlet of the reaction chamber. The flow rate within the reaction chamber is at least 3 m/s, preferably at least 6 m/s and more preferably 10 m/s to 120 m/s and is maintained by a suitable differential pressure. Under these conditions, turbulent flows generally prevail within the reaction chamber.

An advantage of the process according to the invention is that a reactor having a higher space-time yield is attained, together with an equal or better quality of product. The useful life of the reactor (i.e., the production time in relation to idle times, which are necessary for the cleaning of the reactor) can be increased by 40% to 60%, depending upon the isocyanate produced.

The invention is further illustrated but is not intended to be limited by the following examples in which all parts and percentages are by weight unless otherwise specified.

EXAMPLES

The process according to the invention is explained in more detail by the following Example.

Into a mixing tube with a downstream diisocyanate condensation step and a phosgene adsorption tower filled with activated carbon, 5.91 mol/h of phosgene, which had been heated to a temperature of 400° C. at a pressure of 1100 mbar in an upstream heat exchanger, flowed continuously through a nozzle with an external diameter $d_1$ of 1.7 mm and an internal diameter $d_0$ of 1.0 mm, which projected into the mixing tube. At the same time, a mixture of 1.26 moles of gaseous hexamethylene diamine and 1.25 moles nitrogen, heated to 400° C., was passed hourly into the mixing tube through the annular gap between nozzle and mixing tube. The diameter of the mixing tube varied along the longitudinal axis by decreasing down to a diameter $d_2$ of 2.5 mm, at an angle α of 10°, upstream of the nozzle and up to 1.5 mm downstream of the nozzle as shown by length $I_1$ in the FIGURE, and then remaining constant along length $I_2$, which had a length of 17.5 mm. Over the 20 mm length 13 the diameter increased at an angle β of 5° until the diameter $d_3$ was 6.0 mm. The diameter then increased to 10.0 mm as shown by diameter $d_4$. As a result the outwardly flowing amine stream was in a state of accelerated flow. A pressure of approximately 350 mbar was maintained in the mixing tube by applying a vacuum to the outlet from the phosgene adsorption tower. In a condensation step, the hot reaction mixture leaving the reaction chamber was passed through dichlorobenzene, which was maintained at a temperature of 150° C. to 160° C. A selective condensation of diisocyanatohexane took place. The gas mixture, which substantially contained nitrogen, hydrogen chloride and excess phosgene, was passed through the washing step and subsequently freed from phosgene in the adsorption tower. The diisocyanate was recovered in pure form from the washing solution by distillation. The yield of 1,6-diisocyanatohexane was 98.0% of the theoretical yield.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a (cyclo)aliphatic diisocyanate or triisocyanate corresponding to the formula

R—(NCO)$_n$           (I), wherein

R represents a (cyclo)aliphatic hydrocarbon group having up to 15 carbon atoms, provided that there are at least two carbon atoms between two nitrogens, n represents the number 2 or 3, by a) separately heating phosgene and a diamine or triamine corresponding to the formula

R—(NH$_2$)$_n$           (II), to a temperature of 200° C. to 600° C., wherein the amine may optionally be diluted with an inert gas or with the vapors of an inert solvent, b) accelerating the flow of at least one of reactants in the region where the reactants are mixed and c) continuously reacting the reactants in a reaction chamber that does not have moving parts.

2. The process of claim 1 wherein the reactor chamber has a cross-sectional area which is reduced in the region where the reactants are mixed together and widens in the section where the reaction takes place.

3. The process of claim 1 wherein the starting amine is diluted with an inert gas and/or with vapors of an inert solvent.

* * * * *